United States Patent [19]

Holy et al.

[11] Patent Number: 4,585,900
[45] Date of Patent: Apr. 29, 1986

[54] HYDROGENATION OF CARBOXYLIC ACID COMPOUNDS TO ALDEHYDES USING CU/YTO AS CATALYST

[75] Inventors: Norman L. Holy; Abraham P. Gelbein, both of Morristown; Robert Hansen, West Caldwell, all of N.J.

[73] Assignee: Chem Systems Inc., Tarrytown, N.Y.

[21] Appl. No.: 693,246

[22] Filed: Jan. 22, 1985

[51] Int. Cl.$^4$ ............................................. C07C 45/41
[52] U.S. Cl. .................................. 568/435; 568/484; 502/346
[58] Field of Search ................................ 568/435, 484

[56] References Cited

U.S. PATENT DOCUMENTS 3,935,265  1/1976  Feinstein et al. .................... 568/435
4,093,661  6/1978  Trecker et al. .................. 568/435 X
4,328,373  5/1982  Strojny ................................ 568/435

FOREIGN PATENT DOCUMENTS 0101111  2/1984  European Pat. Off. ............ 568/484

Primary Examiner—Bernard Helfin
Attorney, Agent, or Firm—Bert J. Lewen; Henry Sternberg

[57] ABSTRACT

A process for selectively forming aldehydes which comprises hydrogenating a carboxylic acid or a carboxylic acid ester in the presence of an yttrium catalyst activated with copper.

11 Claims, No Drawings

HYDROGENATION OF CARBOXYLIC ACID COMPOUNDS TO ALDEHYDES USING CU/YTO AS CATALYST

BACKGROUND OF THE INVENTION

The catalytic vapor-phase hydrogenation of carboxylic acids and esters to form the corresponding aldehydes is well known. Hydrogenation processes wherein the carboxylic acids and esters are free of hydrogen on the alpha-carbon, such as benzoic acid and methyl benzoate, are taught in U.S. Pat. No. 4,328,373, issued on May 4, 1982 to Dow Chemical Company. The reaction is performed in the presence of metal oxide catalysts such as oxides of yttrium, zirconium, cerium, praseodymium, thorium and uranium supported on alpha-alumina. The first two oxides are most preferred. This work is also described in King et al., "An In Situ Study of Methyl Benzoate and Benzoic Acid Reduction on Yttrium Oxide by Infrared Spectroscopic Flow Reactor," *Journal of Catalysis* 76, 274–284 (1982).

U.S. Pat. No. 4,093,661, issued June 6, 1978 to Union Carbide Corporation, shows the vapor phase disproportionation of lower alkanoate esters of alcohols in the vapor phase to produce aldehydes and ketones over metal oxide catalysts. The preferred catalysts include nickel oxide, zinc oxide, and chromium oxide. The use of other metal oxides, namely, oxides of copper, titanium, vanadium, manganese, iron and cobalt, are also disclosed. It is further taught that the catalyst can be supported on an inert catalyst support such as alumina, silica and carbon.

In U.S. Pat. No. 2,018,350, issued on Oct. 22, 1935 to General Aniline Works, Inc., aldehydes are formed from dicarboxylic acids or their anhydrides with reducing gas in the presence of catalysts such as chromium, iron, copper, manganese, cobalt or their oxides, either alone or mixed with each other. Mixtures of such catalysts with other elements such as lead, cerium, uranium or zinc or oxides of these elements are also generally disclosed. The catalysts include granules of pumice impregnated with iron salts and reduced with hydrogen to prepare benzaldehyde from phthalic anhydride. In addition, a catalyst prepared by reducing fragments of ferric oxide activated with chromium compounds is also described. Other catalysts include copper and iron deposited on granular pumice, a reduced mixture of lead oxide, chromium oxide, and iron oxide, and reduced zinc chromate.

SUMMARY OF THE INVENTION

This invention relates to the catalytic vapor-phase hydrogenation of carboxylic acids and esters to form corresponding aldehydes with an yttrium oxide catalyst treated with copper. The copper treatment of the catalyst has been found to substantially enhance its activity. Such catalysts are particularly useful for converting carboxylic acids and their esters free of hydrogen on their alpha carbon to aldehydes. An example of the reaction for which the catalyst of the invention may be used is the conversion of benzoic acid and methyl benzoate to benzaldehyde. Acids having hydrogen on alpha carbons such as acetic acid and butyric acid are not selectively converted with the copper-treated yttrium oxide catalyst of the invention.

DETAILED DESCRIPTION OF THE INVENTION

Carboxylic acids and esters thereof which can be converted to aldehydes in accordance with the instant invention may be either mono- or dicarboxylic. The esters include aryl and lower alkyl esters of such carboxylic acids. Both aliphatic carboxylic acids and aromatic carboxylic acids may be reacted.

Aromatic carboxylic acids and esters include benzoic, phthalic, isophthalic and terephthalic, as well as alkyl, alkoxy and halo-substituted benzoic acids and esters such as toluic, ethylbenzoic, fluorobenzoic, chlorobenzoic, bromobenzoic and methoxybenzoic. Preferably, the alkyl-substitution would contain from 1 to 6 carbon atoms. Generally, from 1 to 5 alkyl substitutions may be present. Other materials which may be converted include naphthoic, biphenylcarboxylic, anthranoic, trimethylacetic and trifluoroacetic acids and esters.

The yttrium oxide catalyst may be readily prepared as described in the aforementioned U.S. Pat. No. 4,328,373. Generally, a salt of the yttrium compound is heated at a temperature of from 200° to 500° C. under oxidizing conditions to form the corresponding metal oxide. The catalyst may be in the form of pellets or deposited on an inert support material, as for example alumina, silicon carbide, silica, and silica-alumina. Alpha-alumina is preferred.

Generally, from 2 to 20 wt. % of the catalyst is added to the support.

The copper activator, which forms the essence of the catalyst of the invention, may be formed at the same time as the yttrium oxide by means of the reduction of the yttrium and the copper salt simultaneously or the copper oxide may be intimely mixed with the yttrium oxide catalyst. The catalyst comprises from 1 to 15 wt. % copper and from 99 to 85 wt. % yttrium on an elemental basis, preferably from 5 to 10 wt. % of the copper and from 95 to 92 wt. % of the yttrium.

Prior to the reduction of the carboxylic acid or carboxylic acid ester, it is preferable to reduce the catalyst to its metallic form in situ under the reaction conditions.

The hydrogenation reaction may be carried out in a batch or a continuous flow system, as will be readily understood by those skilled in the art. The temperature of the reaction may range from 350° to 500° C., preferably from 400° to 450° C. Pressures of from 200 mm Hg up to a high as 100 atm. may be used, though 1 to 5 atm. is preferred.

The molar ratio of the hydrogen to the carboxylic acid or the carboxylic acid ester may range broadly from 1:1 to 1,000:1, preferably from 20:1 to 200:1. The optimum conditions of temperature, pressure and hydrogen concentration may be readily determined by those skilled in the art, depending on the particular reactant being employed.

The rate of flow of the reactants over the catalyst may range from 0.05 to 2.0 kg acid per kg catalyst/hr., preferably from 0.1 to 1.0 kg acid per kg catalyst/hr.

The following examples further illustrate the instant invention:

EXAMPLE 1

Catalysts were prepared by immersing an alpha-alumina support in an aqueous solution of the catalyst components in the form of nitrates. The solution and support were heated so as to reflux the solution at about 100° C. for two hours. After cooling to room temperature, the excess solution was decanted and the impregnated support was dried at about 120° C. and calcined at 450° C. to produce the metal oxide. A catalyst loading of from about 10 to 20 wt. % of the metal oxide is easily achieved by this procedure. The catalysts in oxide form were reduced in the reactor at reaction conditions prior to the addition of the feed.

In the reactor system, the organic reactant was first placed in a constant temperature vaporizer. The hydrogen reducing gas was preheated and sparged into a reservoir of the heated reactants. From vapor pressure data, the desired concentration of organic reactant in hydrogen was determined. The hydrogen stream, saturated with organic reactant, was immediately heated to the reaction temperature and passed over the catalysts. The products exiting from the reactor were condensed and collected for analysis.

The following table shows the comparative results obtained. Run No. 1 demonstrates the use of an yttrium oxide catalyst in accordance with the prior art. Run No. 2 shows the copper-activated catalyst of the instant invention. In both cases, the catalysts were supported on an alpha-alumina support in the form of ⅛" spheres. In Run No. 2, the percents copper and yttrium were 9% and 91%, respectively, on an elemental basis.

TABLE

| Run # | 1 | 2 |
| --- | --- | --- |
| Reactor Volume (cc) | 17.0 | 17.0 |
| Catalyst Charge (gram) | 14.72 | 14.58 |
| Catalyst | 12.9% $Y_2O_3$ | 13.3% $Y_2O_3$/CuO |
| Residence Time (seconds) | 1.9 | 1.3 |
| F/W (Kg Feed/Kg Catalyst-Hr.) | 0.083 | 0.186 |
| Reactor Temp. °C. | 430 | 428 |
| Feed: Mole % Benzoic Acid in $H_2$ | 1.8 | 2.3 |
| % Conversion of Benzoic Acid | 87.5 | 88 |
| % Molar Selectivity to: | | |
| Benzaldehyde | 92.9 | 94.2 |
| Benzene | 7.1 | 5.8 |
| Toluene | — | — |
| Benzyl Alcohol | — | — |

It will be noted in the above runs that the flow rate in Run No. 2 (using the copper-activated catalyst of the invention) is over twice that of Run No. 1. Despite this, the conversion to benzoic acid in Run No. 2 is comparable and a somewhat higher molar selectivity to benzaldehyde was obtained. This is particularly surprising and clearly shows that the copper-activated catalyst of the invention is far more active than the yttrium catalyst per se.

EXAMPLE 2

A procedure described in Run No. 2 is followed, except that the feed was methyl benzoate. In a 2 hour run at 430° C., and with a feed stream containing 2.0% methyl benzoate, a conversion of 92% of the methyl benzoate is noted. The selectivity to benzaldehyde is 93%.

EXAMPLE 3

The catalyst described in Run No. 2 is employed in a 5 hour run with p-methylbenzoic acid at 425° C. The conversion is 91% and the selectivity to p-methylbenzaldehyde is 94%.

EXAMPLE 4

The catalyst described in Run No. 2 is employed in a 10 hour run with p-tert-butylbenzoic acid at 430° C. The conversion is 95% with a selectivity to p-tert-butylbenzaldehyde of 94%.

EXAMPLE 5

The catalyst described in Run No. 2 is employed in a 4 hour run with 3,5-dimethylbenzoic acid at 435° C. The conversion is 87% at a 2.7% feed, with a selectivity to 3,5-dimethylbenzaldehyde of 93%.

EXAMPLE 6

The catalyst described in Run No. 2 is employed in a 5 hour run with methyl p-methylbenzoate at 430° C. The conversion is 85%, and the selectivity to p-methylbenzaldehyde 95%.

EXAMPLE 7

The catalyst described in Run No. 2 is employed in a 5 hour run with methyl p-methoxybenzoate at 420° C. The conversion is 87%. The selectivity to p-methoxybenzaldehyde and to anisole is 12% and 75%, respectively.

EXAMPLE 8

The catalyst described in Run No. 2 is used in a 2 hour test with p-fluorobenzoic acid at 430° C. The conversion is 75%, and the selectivity to p-fluorobenzaldehyde 89%.

EXAMPLE 9

The catalyst described in Run No. 2 is used in a 4 hour test with 4-phenylbenzoic acid at 433° C. The conversion is 92%, and the selectivity to p-phenylbenzaldehyde 94%.

EXAMPLE 10

The catalyst described in Run No. 2 is used in a 4 hour test of trimethylacetic acid at 423° C. The conversion is 78%, and the selectivity to trimethylacetaldehyde 72%.

EXAMPLE 11

The catalyst described in Run No. 2 is used in a 10 hour test with dimethylterephthalate at 435° C. The conversion is 89%, and the selectivity to terephthalaldehyde 79%.

We claim:

1. A process for the hydrogenation of an aromatic or aliphatic carboxylic acid or an ester thereof to the corresponding aldehyde, said carboxylic acid or ester being free of alpha hydrogens, which comprises reacting said carboxylic acid or ester with at least a 1:1 molar ratio of hydrogen at a temperature in the range of from 300° to 500° C. and at a pressure of from 200 mm Hg to 100 atm. in the presence of an yttrium oxide catalyst which has been treated with copper, said catalyst comprising from 1 to 15 wt. % of copper and from 99 to 85 wt. % of yttrium, on an elemental basis.

2. The process of claim 1 wherein the catalyst is supported on alpha-alumina.

3. The process of claim 1 wherein the reactant is benzoic acid or methyl benzoate and the aldehyde produced therefrom is benzaldehyde.

4. The process of claim 1 wherein the reactant is p-methylbenzoic acid or p-methylbenzoate and the aldehyde is p-methylbenzaldehyde.

5. The process of claim 1 wherein the reactant is p-tert-butylbenzoic acid and the aldehyde is p-tert-butyl-benzaldehyde.

6. The process of claim 1 wherein the reactant is 3,5-dimethylbenzoic acid and the aldehyde is 3,5-dimethylbenzaldehyde.

7. The process of claim 1 wherein the reactant is methyl p-methoxybenzoate and the aldehyde is p-methoxybenzaldehyde and anisole.

8. The process of claim 1 wherein the reactant is p-fluorobenzoic acid and the aldehyde is p-fluorobenzaldehyde.

9. The process of claim 1 wherein the reactant is 4-phenylbenzoic acid and the aldehyde is p-phenylbenzaldehyde.

10. The process of claim 1 wherein the reactant is trimethylacetate and the aldehyde is trimethylacetaldehyde.

11. The process of claim 1 wherein the reactant is dimethylterephthalate and the aldehyde is terephthalaldehyde.

* * * * *